United States Patent
Arora et al.

[11] Patent Number: 5,948,440
[45] Date of Patent: Sep. 7, 1999

[54] MODIFIED RELEASE MATRIX FORMULATION OF CEFACLOR AND CEPHALEXIN

[75] Inventors: Jagdish Arora, Chaudlgarh; Girish Jain, Delhi; Himadri Sen, Haryana, all of India

[73] Assignee: Ranbaxy Laboratories Limited, New Delhi, India

[21] Appl. No.: 08/992,151

[22] Filed: Dec. 17, 1997

[51] Int. Cl.⁶ .............................. A61K 9/22; A61K 47/38
[52] U.S. Cl. ..................... 424/468; 424/499; 424/488; 514/964
[58] Field of Search .................................. 424/484, 468, 424/499, 488; 514/964

[56] References Cited

U.S. PATENT DOCUMENTS

| | | |
|---|---|---|
| 3,065,143 | 4/1962 | Christenson et al. . |
| 4,250,166 | 2/1981 | Maekawa et al. . |
| 4,259,314 | 3/1981 | Lowey . |
| 4,369,172 | 1/1983 | Schor et al. . |
| 4,557,925 | 12/1985 | Lindahl et al. . |
| 4,704,285 | 11/1987 | Alderman . |
| 4,713,247 | 12/1987 | Sakamoto et al. . |
| 4,734,285 | 3/1988 | Alderman . |
| 4,756,911 | 7/1988 | Drost et al. . |
| 4,762,951 | 2/1988 | Panoz et al. . |
| 4,795,327 | 1/1989 | Gaylord et al. . |
| 4,871,548 | 10/1989 | Edgren et al. . |
| 4,919,938 | 4/1990 | Lovegrove et al. . |
| 4,968,508 | 11/1990 | Oren et al. . |
| 4,983,398 | 1/1991 | Gaylord et al. . |
| 5,051,262 | 9/1991 | Panoz et al. . |

FOREIGN PATENT DOCUMENTS

| | | |
|---|---|---|
| 75340/87 | 1/1988 | Australia . |
| 27305/88 | 4/1991 | Australia . |
| 58-92615 | 6/1983 | Japan . |

*Primary Examiner*—Edward J. Webman
*Attorney, Agent, or Firm*—Jayadeep R. Deshmukh

[57] ABSTRACT

A pharmaceutical composition in the form of a tablet for controlled release of an active ingredient comprises cefaclor, cephalexin, or their pharmaceutically acceptable hydrates, salts, or esters as active ingredient, and a mixture of hydrophilic polymers of different viscosity grades selected from the group consisting of at least one hydroxypropyl methylcellulose and at least one hydroxypropylcellulose. The composition optionally also contains one or more of a water soluble or water dispersible diluent. The quantities of the hydrophilic polymers and water soluble or water dispersible diluent are such that the therapeutically effective active ingredient is released at a rate suitable for twice daily administration of the pharmaceutical composition to human subjects. The tablets may also be coated with a rapidly dissolving water soluble polymeric film coat. In a preferred embodiment, the composition comprises about 50% to about 90% by weight of cefaclor, cephalexin, or their pharmaceutically acceptable hydrates, salts, or esters, and about 5% to about 35% of a mixture of hydrophilic polymers of different grades, wherein the hydrophilic polymers comprise about 0.1% to about 20% by weight of hydroxypropyl methylcellulose and about 0.1% to about 20% by weight of hydroxypropyl cellulose.

15 Claims, 1 Drawing Sheet

MODIFIED RELEASE MATRIX FORMULATION OF CEFACLOR AND CEPHALEXIN

FIELD OF THE INVENTION

This invention relates to a pharmaceutical composition of modified release tablets comprising cefaclor or cephalexin, or their pharmaceutically acceptable hydrates, salts, or esters as active ingredient, and a mixture of hydrophilic polymers of different viscosity grades selected from the group consisting of at least one hydroxypropyl methylcellulose and at least one hydroxypropylcellulose. Optionally, the composition also contains one or more of a water soluble and/or water dispersible diluent, wherein the quantities of the hydrophilic polymers and water soluble and/or water dispersible diluents are such that the therapeutically effective active ingredient is released at a rate suitable for twice-daily administration of the pharmaceutical composition to human subjects. Optionally, the tablets may be coated with a rapidly dissolving water soluble polymer film coat.

BACKGROUND OF THE INVENTION

The use of hydrophilic polymers to produce sustained or modified release pharmaceutical compositions is known in the art. For modified release solid dosage forms comprising a drug dispersed uniformly in hydrophilic polymers, release of the drug is controlled primarily by diffusion of the drug, or by surface erosion of the hydrophilic polymers into the surrounding medium, or by a combination of the two processes. Control of the rate of release benefits therapy by producing constant blood levels of the active ingredient and by decreasing the frequency of administration, thereby improving patient compliance to the dosage regimen. The present invention provides a pharmaceutical composition of modified release tablets of cefaclor or cephalexin suitable for twice-daily administration to human subjects.

Several controlled drug delivery system adapted for the delivery of cefaclor or cephalexin are known in the prior art.

U.S. Pat. No. 4,968,508 discloses a sustained release matrix tablet comprising from about 0.1% by weight to 90% by weight of cefaclor, from about 5% by weight to 29% by weight of a hydrophilic polymer, and from about 0.5% by weight to about 25% by weight of an acrylic polymer which dissolves in the pH range from about 5.0 to 7.4, with the proviso that the total weight of the polymers is less than 30% by weight of the formulation. Although a specific cefaclor formulation is described, the description in the patent suggests that the formulation is suitable for any drug and is particularly suitable for cephalexin and cefaclor.

U.S. Pat. No. 4,919,938 discloses a sustained release pharmaceutical composition in tablet form consisting essentially of a core matrix containing 20% to 60% by weight of a hydroxypropylmethylcellulose gelling agent, 0.41% to 20% by weight of (+)-trans-1a,2,3,4a,5,6-hexahydro-9-hydroxy-4-(1-propyl)-4H-naphth [1,2-b]-1,4-oxazine hydrochloride, 2.08 to 12.5% by weight of buffering agent and suitable pharmaceutically acceptable excipients. A coating of a slowly soluble water permeable ethylcellulose polymer surrounds the core matrix.

U.S. Pat. No. 4,983,398 discloses a therapeutically active composition comprising a mixture of a therapeutically active medicament and a carrier base material, wherein the carrier base material consists essentially of one or more water-soluble, non-ionic cellulose ethers, wherein at least one of the cellulose ethers is a hydroxypropyl methylcellulose having a number average molecular weight of at least 50,000, and an alkali metal carboxylate. The carrier base comprises less than 30% by weight of the total weight of the composition.

U.S. Pat. No. 4,369,172 discloses a carrier base material combined with a therapeutically active medicament shaped and compressed to a solid unit dosage form having a regular and prolonged release pattern upon administration. The carrier base material is hydroxypropyl methylcellulose, or a mixture of hydroxypropyl methylcellulose and up to 30% by weight of a mixture of ethylcellulose and/or up to 30% by weight of the mixture of sodium carboxymethylcellulose, and wherein the hydroxypropyl methylcellulose has a hydroxypropyl content of 9–12% weight and a number average molecular weight of less than 50,000.

U.S. Pat. No. 4,713,247 discloses a long-acting formulation of cefaclor which comprises a mixture of a non-enteric coated component of cefaclor as a rapid-release component and an enteric coated component of cefaclor as a slow-release component at a ratio of 4:6 based upon cefaclor potency. The rapid release component contains at least one additive selected from the group consisting of lactose, sucrose, D-mannitol, corn starch, wheat starch and low-substituted hydroxypropylcellulose in an amount of up to 75 weight % based on the whole rapid release component. The slow release component contains at least one additive selected from the group consisting of lactose, sucrose, D-mannitol, corn starch, wheat starch and low-substituted hydroxypropylcellulose in an amount of up to 75 weight % based on the whole slow release component and is coated with an enteric coating film soluble in the pH range of 5.0 to 7.0.

U.S. Pat. No. 4,250,166 discloses a long-acting cephalexin preparation which comprises normal (i.e., plain, quick r?,leasing) cephalexin which dissolves rapidly in the stomach, and coated particulate cephalexin which does not dissolve in the stomach but-dissolves rapidly in the upper intestine. The coated portion is coated with a copolymer of methylmethacrylate and methacrylic acid which dissolves at a pH of from 5.5 to 6.5. The potency ratio of the normal cephalexin to the coated portion is between 40:60 and 25:75.

U.S. Pat. No. 4,557,925 discloses a controlled release pharmaceutical tablet comprising a drug and a coating applied thereon. The coating comprises a film-forming forming polymer which is insoluble in water and gastrointestinal fluids and consists essentially of a terpolymer of polyvinylchloride, polyvinyl acetate and polyvinyl alcohol, and a water soluble pore creating material randomly distributed in the terpolymer coating. The pore creating substance is present in an amount of one part to 35 parts for each one to ten parts of terpolymer.

U.S. Pat. No. 4,726,951 discloses a pharmaceutical composition for oral administration with selectively adjustable programmed release and controlled absorption, comprising miniaturized granules obtained by high to very high compression. The pharmaceutical composition comprises miniaturized granules (a) containing pH control agents, (b) coated with excipients determining the slow penetration of digestive liquids, and/or (c) coated with a very thin layer of liquids or mixture of such granules, with the relative proportion of (a), (b) and (c) adjusted to give the desired release of the active ingredient. Cephalexin is one of the active ingredients disclosed.

U.S. Pat. No. 5,051,262 discloses a delayed action programmed release pharmaceutical preparation of one or more medicament units suitable for oral administration, each unit comprising an inert core surrounded by at least one inner layer and one or more inert outer coatings. At least one of the inner layers comprises an active medicament, which has a solubility which varies with pH and is either basic or acidic, and at least one pH adjuster. The pH adjuster is an organic acid or organic acid salt if the medicament is basic, or an inorganic base or basic salt if the medicament is acidic. The pH adjuster is present in an amount sufficient to ensure that the rate of dissolution of the medicament is substantially independent of the pH of the environment in which dissolution occurs. Cephalexin is described as one of the possible medicaments.

SUMMARY OF THE INVENTION

This invention is directed to a pharmaceutical composition of modified release tablets comprising cefaclor or cephalexin, or their pharmaceutically acceptable hydrates, salts, or esters, as the active ingredient, and a mixture of hydrophilic polymers of different viscosity grades selected from the group consisting of at least one hydroxypropyl methylcellulose and at least one hydroxypropylcellulose; and, optionally, one or more water soluble and/or water dispersible diluents wherein the quantities of the hydrophilic polymers and water soluble and/or water dispersible diluents are such that the therapeutically effective active ingredient is released at a rate suitable for twice daily administration of the pharmaceutical composition to human subjects. The tablets may be coated with a rapidly dissolving water soluble film coating.

DETAILED DESCRIPTION OF THE INVENTION

Figure 1:
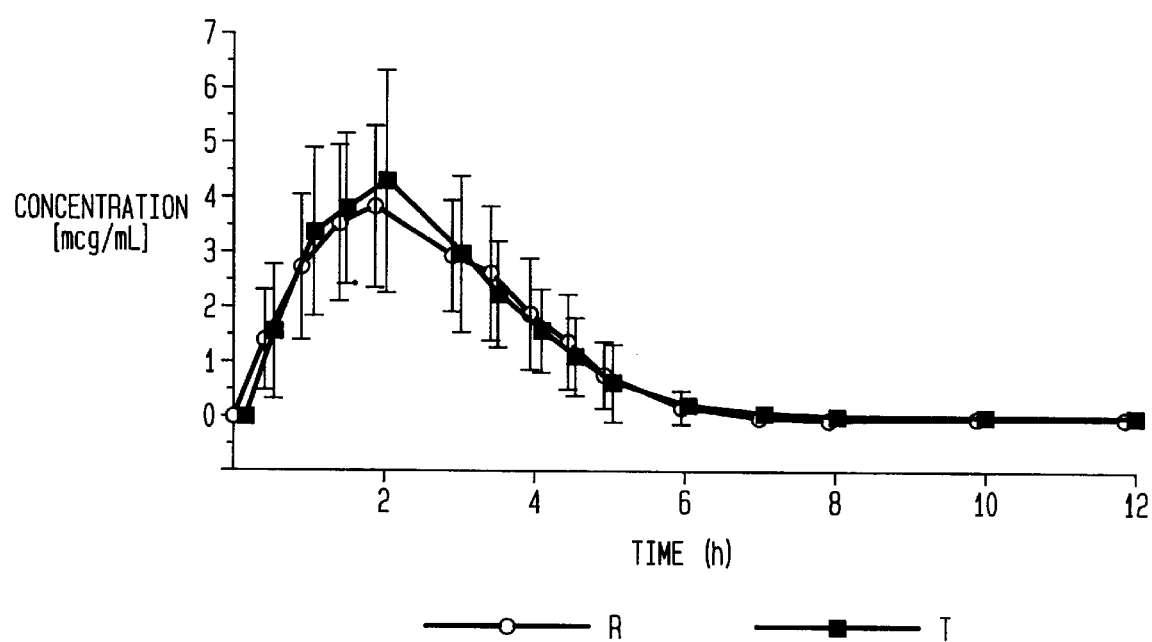
FIG. 1 is a graph illustrating the release over time of cefaclor into the bloodstream for a composition of the present invention and a reference formulation.

The composition of this invention is in the form of a matrix tablet comprising the active ingredient, hydrophilic polymers, water soluble and/or water dispersible diluents and pharmaceutically acceptable tablet excipients. The tablet may be optionally coated with a rapidly dissolving water soluble polymer film coat.

According to the present invention the pharmaceutical composition contains cefaclor or cephalexin, or their pharmaceutically acceptable hydrates, salts or esters as active ingredient. The cefaclor or cephalexin or their pharmaceutically acceptable salts or esters may be present in an amount from about 50% to 90% by weight, more preferably, from about 60% to 85% by weight, of the total weight of the pharmaceutical composition.

Further, the cefaclor or cephalexin or their pharmaceutically acceptable hydrates, salts, or esters may be present in an amount from 175 mg to 1000 mg per tablet.

According to the present invention, the pharmaceutical composition contains a mixture of hydrophilic polymers of different viscosity grades selected from the group consisting of hydroxypropyl methylcellulose and hydroxypropylcellulose. For the purposes of this patent application, hydrophilic polymers may be characterized by their viscosities in a 2% w/w aqueous solution as low viscosity (less than about 1,000 cPs), medium viscosity (about 1,000 cPs to about 10,000 cPs), and high viscosity (greater than about 10,000 cPs).

Hydroxypropyl methylcellulose polymers which are hydrophilic in nature and which may be used in the present invention are of different viscosity grades such as those available under the brand name Methocel™ available from Dow Chemical Co. Examples of hydroxypropyl methylcellulose polymers of a low viscosity grade include those available under the brand names Methocel E5, Methocel E-15 LV, Methocel E50 LV, Methocel K100 LV and Methocel F50 LV whose 2% by weight aqueous solutions have viscosities of 5 cPs, 15 cPs, 50 cPs, 100 cPs and 50 cPs, respectively. Examples of hydroxypropyl methylcellulose polymers having medium viscosity include those available under the brand names Methocel E4M and Methocel K4M both of whose 2% by weight aqueous solutions have a viscosity of 4000 cPs. Examples of hydroxypropyl methylcellulose polymers having high viscosity include those available under the brand names Methocel K15M and Methocel K100M whose 2% by weight aqueous solutions have viscosities of 15,000 cPs and 100,000 cPs, respectively. The hydroxypropyl methylcellulose polymers may be present in the pharmaceutical composition of the present invention in an amount from about 0.1% to 20% by weight.

The hydroxypropylcellulose polymers that may be used in the present invention include, for example, polymers available under the brand names Klucel™ and HPC™, available from Aqualon and Nippon Soda Co. Hydroxypropylcellulose polymers available under the brand names Klucel EF, Klucel LF, Klucel JF and Klucel GF whose 2% by weight aqueous solutions have viscosities less than 1000 cPs and are examples of low viscosity hydrophilic polymers. Hydroxypropylcellulose polymer available under the brand name Klucel ME whose 2% by weight aqueous solution has a viscosity in the range from 4,000–6,500 cPs is a medium viscosity hydrophilic polymers. Hydroxypropylcellulose polymers available under the brand names HPC-SL, HPC-L, and HPC-M whose 2% by weight aqueous solutions have viscosities of 3–6 cPs, 6–10 cPs, and 150–400 cPs, respectively, are examples of low viscosity hydrophilic polymers, while HPC-H has a viscosity of 1,000–4000 cPs and is an example fo a medium viscosity hydrophilic polymer. The hydroxypropylcellulose polymers may be present in an amount from about 0.1% to 15% by weight.

In a preferred embodiment of the present invention, the pharmaceutical composition comprises from about 50% to 90% by weight of cefaclor or cephalexin or their pharmaceutically acceptable hydrates, salts, or esters, and about 5% to 35% by weight of a mixture of hydrophilic polymers of different viscosity grades comprising from about 0.1% to 20% by weight hydroxypropyl methylcellulose and about 0.1% to 20% by weight of hydroxypropylcellulose. Preferably, the composition also contains about 1% to 15% by weight of one or more water soluble and/or water dispersible diluents.

In a more preferred embodiment of the present invention, the pharmaceutical composition comprises from about 60% by weight to 85% by weight of cefaclor or cephalexin or their pharmaceutically acceptable hydrates, salts, or esters, and about 5% to 30% by weight of hydrophilic polymers comprising a mixture of a medium and/or a high viscosity grade hydroxypropyl methylcellulose in an amount from about 0.5% to 5% by weight, a low viscosity grade hydroxypropyl methylcellulose in an amount from about 4% to 12% by weight, and a low viscosity grade hydroxypropylcellulose in an amount from about 2% to 15% by weight of the total weight of the composition.

According to the present invention the pharmaceutical composition may contain one or more of a water soluble and/or water dispersible diluent. Preferably the water soluble and/or dispersible diluents may be present in an amount from about 1% to 15% by weight of the total weight of the composition. Examples of water soluble diluents that may be used in the present invention include, but are not limited to, lactose, calcium sulfate, mannitol, dextrates, dextrin, dextrose, sucrose and the like.

Water dispersible diluents refer to water insoluble pharmaceutical excipients which disperse readily in water. Examples of water dispersible diluents that may be used in the present invention include, but are not limited to, cellulose based diluents such as microcrystalline cellulose and powdered cellulose; various starches such as corn starch and pregelatinized starch; clays or clay minerals such as kaolin, bentonite, attapulgite, and the like. In one preferred embodiment, the water soluble diluent is lactose in amounts from about 1% to 15% by weight, more preferably from 2 to 8% by weight. In another preferred embodiment, the water dispersible diluent is microcrystalline cellulose present in amounts from about 1% to 15% by weight, more preferably from about 1% to about 7% by weight.

In addition to the above ingredients, pharmaceutical grade magnesium stearate/stearic acid as a glidant, talc as an anti-adherent, and silicon dioxide (Aerosil-200) as a lubricant are included in the matrix formulation. Preferably, magnesium stearate/stearic acid, talc and silicon dioxide are present in amounts in the range of 0.2% to 5% by weight either alone or in combination.

According to a process for making the composition of the present invention, the cefaclor or cephalexin or their pharmaceutically acceptable hydrates, salts, or esters, the hydrophilic polymers of different viscosity grades consisting of at least one hydroxypropyl methylcellulose and at least one hydroxypropyl cellulose; and, optionally, one or more water soluble and/or water dispersible diluents are either mixed together with lubricants and the blend is directly compressed into tablets, or are granulated by compaction followed by sieving, and the granules so obtained are compressed into tablets.

Preferably, an Octablender™ apparatus is used for blending the cefaclor/cephalexin and hydrophilic polymers, with optimum mixing time being 10–20 minutes and the blended powder is compacted in a roll-compactor and milled using cadmill, multimill or oscillating granulator to obtain granules wherein fines contribute to a fraction having a size less than 250 microns. The fines present in the granules in which the drug cefaclor/cephalexin is present in a finely divided state has a significant influence in the release profile of the drug. The final mix ready for compression may contain 20 to 45% by weight, preferably from about 20% to 35% by weight of fines.

The advantage of the above mentioned process of the present invention is that it is free of any disadvantages associated with granulation by aqueous or non-aqueous vehicles used conventionally. The drugs cefaclor and cephalexin, which are sensitive to moisture and heat, can be effectively processed without any difficulty by the process of the present invention. In the pharmaceutical industry, particularly, much emphasis is directed to limit the residual solvents for the safety of the patients and such problems of residual organic solvents are eliminated by the process of the invention.

The tablets may be optionally coated with a rapidly dissolving water soluble film coat. The tablets may be coated to a weight build-up of about 1% by weight to 10% by weight, preferably from about 1% to about 4% by weight. Preferably, the coating composition contains a flavoring agent in order to mask the taste and odor of the active ingredient.

The modified release matrix formulation prepared according to the present invention is not a mere admixture but has properties different from the sum total of the properties of its ingredients.

The present invention is illustrated by the following examples.

EXAMPLE 1

This example illustrates the preparation of controlled release tablets of cefaclor having a composition as given in Table 1.

TABLE 1

| Ingredient | Weight (mg/tablet) | % w/w |
| --- | --- | --- |
| Cefaclor Monohydrate | 409.0 | 75.17 |
| Methocel K4M CR Premium | 15.0 | 2.58 |
| Hydroxy Propyl Cellulose-L | 70.0 | 12.06 |
| Methocel E-5 Premium | 50.0 | 8.62 |
| Lactose | 26.0 | 4.48 |
| Magnesium Stearate | 5.0 | 0.86 |
| Talc | 3.0 | 0.51 |
| Aerosil-200 | 2.0 | 0.34 |
| Total | 580.0 | 100% |

Cefaclor, the hydrophilic polymers and lactose were screened through a fine sieve and mixed with half of the magnesium stearate and talc. The mixture obtained was compacted and then milled. The sized granules were blended with the fines and the remaining lubricants followed by compression into tablets.

The tablets were coated in Ganscota/Neocota™ apparatus using the coating composition as given in Table 2. The percent build-up was 2.5% by weight.

TABLE 2

| Ingredient | % w/w |
| --- | --- |
| Hydroxypropyl Methylcellulose (5–6 cps) | 6.45 |
| PEG-400 | 0.85 |
| Titanium Dioxide | 1.08 |
| Sunset Yellow | 0.29 |
| Talc | 0.43 |
| Water | 90.9 |

The coated tablets were tested for dissolution in 900 ml of 0.1 N hydrochloric acid for one hour, after which the dissolution medium was changed to a pH 6.8 mixed phosphate buffer (900 ml).

The dissolution medium (pH 6.8 phosphate buffer) was replaced with fresh medium every hour thereafter.

Tablets were placed into a 40-mesh basket (USP Apparatus—Type I) and were rotated at 100 rpm. Spectrophotometric methodology (at 264 nm) was used for estimation of drug release. The results are given in Table 3:

TABLE 3

| Time (min) | Percent Cefaclor released (%) |
| --- | --- |
| 60 | 43.46 |
| 120 | 69.06 |
| 180 | 88.91 |
| 240 | 101.53 |

EXAMPLE 2

This example illustrates the preparation of controlled release tablets of cefaclor having a composition as given in Table 4.

TABLE 4

| Ingredient | Weight (mg/tablet) | % w/w |
|---|---|---|
| Cefaclor Monohydrate | 546.32 | 70.95 |
| Methocel K4M CR Premium | 14.00 | 1.82 |
| Hydroxy Propyl Cellulose-L | 93.33 | 12.12 |
| Methocel E-5 Premium | 66.67 | 8.66 |
| Lactose | 36.34 | 4.72 |
| Magnesium Stearate | 6.67 | 0.87 |
| Talc | 4.00 | 0.52 |
| Aerosil-200 | 2.67 | 0.34 |
| Total | 770.00 | 100% |

The cefaclor, hydrophilic polymers, lactose and the lubricants were mixed together and the blend so obtained was compressed into tablets. The tablets were then coated with a hydroxypropyl methylcellulose based 12% by weight aqueous coating system (OPADRY®OY of Colorcon, USA) to a weight build-up of 2.5% by weight. The tablets were tested for dissolution as described in Example 1. The results are given in Table 5.

TABLE 5

| Time (min) | Cumulative percent Cefaclor released |
|---|---|
| 60 | 50.83 |
| 120 | 80.06 |
| 180 | 100.61 |

EXAMPLE 3

This example illustrates the preparation of controlled release tablets of cephalexin having a composition as given in Table 6.

TABLE 6

| Ingredient | Weight (mg/tablet) | % w/w |
|---|---|---|
| Cephalexin Monohydrate | 408.0 | 70.31 |
| Methocel K4M CR Premium | 15.0 | 2.59 |
| Hydroxy Propyl Cellulose-M | 50.0 | 8.62 |
| Methocel E-5 Premium | 50.0 | 8.62 |
| Lactose | 49.0 | 8.45 |
| Magnesium Stearate | 5.0 | 0.86 |
| Talc | 3.0 | 0.52 |
| Total | 580.0 | 100% |

The tablets were prepared and the uncoated tablets were tested for dissolution as described in Example 1 except that only aliquots and not all of the pH 6.8 phosphate buffer were withdrawn and replaced with fresh sample every hour. The results are given in Table 7.

TABLE 7

| Time (min) | Cumulative percent cephalexin released (%) |
|---|---|
| 60 | 44.2 |
| 120 | 59.8 |
| 180 | 77.5 |
| 240 | 92.5 |
| 300 | 95.6 |

EXAMPLE 4

This example illustrates the preparation of controlled release tablets of cephalexin having a composition as given in Table 8.

TABLE 8

| Ingredient | Weight (mg/tablet) | % w/w |
|---|---|---|
| Cephalexin Monohydrate | 801.53 | 77.07 |
| Methocel K4M CR Premium | 15.00 | 1.44 |
| Hydroxyl Propyl Cellulose-M | 45.00 | 4.33 |
| Methocel E-5 Premium | 115.00 | 11.06 |
| Avicel 101 PH | 40.47 | 3.89 |
| Magnesium Stearate | 10.50 | 1.01 |
| Talc | 7.50 | 0.72 |
| Aerosil 200 | 5.00 | 0.48 |
| Total | 1,040.00 | 100% |

The tablets were prepared as described in Example 1. The tablets were coated to a weight build-up of 1.5% by weight using the coating composition given in Table 9.

TABLE 9

| Ingredient | % w/w |
|---|---|
| Hydroxypropyl Methylcellulose E-5 | 7.50 |
| Polyethylene glycol 400 | 0.75 |
| Ethylvanillin | 0.75 |
| Titanium dioxide | 0.30 |
| Talc | 0.75 |
| Water | 89.95 |

The coated tablets tested for dissolution as described in Example 1 and the results are given in Table 10.

TABLE 10

| Time (min) | Cumulative percent cephalexin released (%) |
|---|---|
| 30 | 30.95 |
| 60 | 57.05 |
| 120 | 73.88 |
| 180 | 88.92 |
| 240 | 96.60 |

A study was conducted for bioequivalence between a cefaclor test formulation (T) in accordance with the composition of this invention and a reference product (R) already being marketed, Distaclor™ MR, both having a cefaclor content equivalent to 375 mg. Twenty three healthy male volunteers were selected for a randomized, two way crossover, bio-equivalence study in which each volunteer was administered a dose of the drug with 240 ml of water. The volunteers fasted overnight before taking the drug.

FIG. 1 shows plots of blood level concentration of cefaclor for the reference product (R) and the composition of the present invention (T). The test formulation (T) was found to be bioequivalent to the reference product (R) as per the UK-MCA guidelines.

While the invention has been described by reference to specific embodiments, this was for purposes of illustration only. Numerous alternative embodiments will be apparent to those skilled in the art and are considered to be within the scope of the invention.

What is claimed is:

1. A pharmaceutical composition for controlled release of an active ingredient, said composition comprising cefaclor, cephalexin, or their pharmaceutically acceptable hydrates, salts, or esters has the active ingredient, and a mixture of hydrophilic polymers of different viscosity grades, said hydrophilic polymers being selected from the group consisting of at least one hydroxypropyl methylcellulose and at least one hydroxypropylcellulose, wherein said composition comprises about 60% to about 85% by weight of said active ingredient, and about 5% to about 30% by weight of said mixture of hydroghilic polymers of different viscosity grades, wherein said mixture of hydrophilic polymers comprises a medium or a high viscosity grade hydroxypropyl methylcellulose in an amount from 0.5% to about 5% by weight, a low viscosity grade hydroxypropyl methylcellulose in an amount from about 4% to about 12% by weight, and a low viscosity grade hydroxypropylcellulose in an amount from 2% to about 15% by weight.

2. The composition of claim 1 which further contains at least one water soluble or water dispersible diluent.

3. The composition of claim 1 in the form of a tablet.

4. The composition of claim 1 wherein the active ingredient is present in an amount from about 175 mg to about 1000 mg per unit dose.

5. The composition of claim 1 which further contains about 1% to about 15% by weight of a water soluble or water dispersible diluent.

6. The composition of claim 5 wherein the diluent is lactose.

7. The composition of claim 6 wherein the amount of lactose is from about 2% to about 8% by weight.

8. The composition of claim 5 wherein the diluent is microcrystalline cellulose.

9. The composition of claim 8 wherein the amount of microcrystalline cellulose is from about 1% to about 7% by weight.

10. The composition of claim 1 further comprising magnesium stearate, stearic acid, talc, silicon dioxide, alone or in combination, in amounts from about 0.2% to about 5% by weight each.

11. The composition of claim 1 in the form of a tablet wherein the tablet is coated with a water soluble polymeric film coating.

12. The composition of claim 11 wherein said coating comprises hydroxypropyl methylcellulose at a weight build-up of about 1% to about 4% by weight of said tablet.

13. A process for the preparation of the pharmaceutical composition of claim 1, comprising mixing together the active ingredient and the hydrophilic polymers of different viscosity grades together with at least one lubricant to form a blend, and compressing the blend into tablets.

14. The process of claim 13 further comprising compacting the blend into granules, and sifting the granules, after which the granules are compressed into tablets.

15. The process of claim 13 further comprising coating the tablets with a fast dissolving film of a water soluble polymer.

* * * * *